(12) United States Patent
Kurzweil et al.

(10) Patent No.: US 9,198,617 B2
(45) Date of Patent: Dec. 1, 2015

(54) HARNESS WITH SENSORS

(71) Applicant: Medicomp, Inc., Melbourne, FL (US)

(72) Inventors: Raymond C. Kurzweil, Newton, MA (US); Paul Albrecht, Bedford, MA (US); Brandon Craft, Reisterstown, MD (US); Lucy Gibson, Belmont, MA (US); Mark Lutwyche, Reisterstown, MD (US); Vishal Dua, Columbia, MD (US); Aaron Kleiner, West Newton, MA (US); Michelle Daniels, Raleigh, NC (US)

(73) Assignee: Medicomp, Inc., Melbourne, FL (US)

( * ) Notice: Subject to any disclaimer, the term of this patent is extended or adjusted under 35 U.S.C. 154(b) by 116 days.

(21) Appl. No.: 13/952,332

(22) Filed: Jul. 26, 2013

(65) Prior Publication Data
US 2014/0031705 A1    Jan. 30, 2014

Related U.S. Application Data

(63) Continuation of application No. 11/749,253, filed on May 16, 2007, now Pat. No. 8,527,028.

(51) Int. Cl.
| *A61B 5/04* | (2006.01) |
| *A61B 5/00* | (2006.01) |
| *A61B 5/0408* | (2006.01) |
| *A61B 5/01* | (2006.01) |
| *A61B 5/0295* | (2006.01) |

(Continued)

(52) U.S. Cl.
CPC ............. *A61B 5/6831* (2013.01); *A61B 5/01* (2013.01); *A61B 5/0295* (2013.01); *A61B 5/0402* (2013.01); *A61B 5/0408* (2013.01); *A61B 5/08* (2013.01); *A61B 5/6804* (2013.01)

(58) Field of Classification Search
CPC ...... A61B 5/04; A61B 5/0402; A61B 5/0408; A61B 5/04085; A61B 5/0535; A61B 5/6804; A61B 5/6805; A61B 5/6823; A61B 5/6831; A61B 2562/0209; A61B 2562/0271
USPC .................. 600/382, 388–390, 393, 509, 301
See application file for complete search history.

(56) References Cited

U.S. PATENT DOCUMENTS

| 3,409,007 A | 11/1968 | Fuller |
| 4,243,052 A | 1/1981 | Bailey |

(Continued)

FOREIGN PATENT DOCUMENTS

| CA | 2324713 | 4/2001 |
| GB | 2388196 | 11/2003 |

(Continued)

*Primary Examiner* — Lee S Cohen
*Assistant Examiner* — Erin M Cardinal
(74) *Attorney, Agent, or Firm* — Mark R. Malek; Kelly G. Swartz; Widerman Malek, P.L.

(57) ABSTRACT

A garment for ambulatory, physiological monitoring of a patient includes a belt, having first and second end portion with closures at the end portions to wrap around a user's chest, a strap having a first end coupled to a portion of the belt with the strap having a second end, a pair of shoulder strap portions each shoulder strap portion having a first end coupled together at the second end of the strap and a second end, and a back portion that joins the second ends of the pair of shoulder strap portions, with at least one of the belt, strap portions and back portion having an accommodation for carrying a sensor. Other embodiments are described.

7 Claims, 15 Drawing Sheets

(51) Int. Cl.
  *A61B 5/0402*  (2006.01)
  *A61B 5/08*  (2006.01)

(56) References Cited

U.S. PATENT DOCUMENTS

| | | | |
|---|---|---|---|
| 4,922,911 A | | 5/1990 | Wada et al. |
| 4,966,154 A | * | 10/1990 | Cooper et al. ............... 600/484 |
| 5,353,793 A | | 10/1994 | Bornn |
| 5,445,149 A | | 8/1995 | Rotolo et al. |
| 6,047,203 A | | 4/2000 | Sackner et al. |
| 6,065,154 A | | 5/2000 | Hulings et al. |
| 6,102,856 A | | 8/2000 | Groff et al. |
| 6,179,786 B1 | | 1/2001 | Young |
| 6,205,346 B1 | | 3/2001 | Akiva |
| 6,341,229 B1 | | 1/2002 | Akva |
| 6,341,504 B1 | | 1/2002 | Istook |
| 6,477,397 B1 | | 11/2002 | Ronkainen et al. |
| 6,551,252 B2 | | 4/2003 | Sackner et al. |
| 6,668,380 B2 | | 12/2003 | Marmaropoulos et al. |
| 6,755,795 B2 | | 6/2004 | Marmaropoulos et al. |
| 6,807,438 B1 | | 10/2004 | Brun Del Re et al. |
| 6,912,414 B2 | | 6/2005 | Tong |
| 6,930,608 B2 | | 8/2005 | Grajales et al. |
| 7,173,437 B2 | | 2/2007 | Hervieux |
| 7,308,294 B2 | | 12/2007 | Hassonjee |
| 7,670,295 B2 | | 3/2010 | Sackner |
| 7,795,335 B2 | | 9/2010 | Okuzaki |
| 8,224,418 B2 | | 7/2012 | Birnbaum |
| 8,527,028 B2 | * | 9/2013 | Kurzweil et al. ............. 600/388 |
| 2003/0212319 A1 | | 11/2003 | Magill |
| 2005/0049515 A1 | | 3/2005 | Misczynski |
| 2005/0059896 A1 | | 3/2005 | Drakulic |
| 2005/0119701 A1 | | 6/2005 | Lauter |
| 2005/0228234 A1 | | 10/2005 | Yang |
| 2006/0069320 A1 | | 3/2006 | Wolf |
| 2006/0135863 A1 | * | 6/2006 | Birnbaum et al. ............ 600/388 |
| 2008/0015454 A1 | * | 1/2008 | Gal ............................... 600/509 |

FOREIGN PATENT DOCUMENTS

| | | |
|---|---|---|
| WO | WO0230279 | 4/2002 |
| WO | WO 2005053532 | 6/2005 |
| WO | WO 2006111875 A1 | 10/2006 |

* cited by examiner

HARNESS WITH SENSORS

RELATED APPLICATIONS

The present application is a continuation of U.S. patent application Ser. No. 11/749,253 titled Harness with Sensors and filed on the 16th of May, 2007, now issued as U.S. Pat. No. 8,527,028 on Sep. 3, 2013, the entire contents of which are incorporated herein by reference.

BACKGROUND

The present invention relates to physiological monitoring and in particular to ambulatory physiological monitoring.

Heart disease is a leading cause of death in the United States. Some patients would benefit from long-term, e.g., ECG monitoring outside of a clinical setting for many heart conditions, including, for example, atrial fibrillation and myocardial ischemia, which may occur episodically. Some episodes may occur without patient symptoms. Myocardial ischemia, if persistent and serious, can lead to myocardial infarction (heart attack). During a myocardial infarction, electrophysiological changes are usually seen on the ECG. For accurate diagnosis and effective treatment of many episodic heart conditions it is useful to know the frequency and duration of such episodes, in a timely manner.

In conventional long-term ECG monitoring, such as with continuous Holter monitors or event monitors, the skin is prepared by a technician. Chest hair may be shaved or clipped from men. The skin is abraded to remove dead skin cells, and cleaned. Abrading often leaves the skin irritated. A technician trained in electrode placement applies the electrodes to the skin with an adhesive. The monitor can be worn for up to a month.

Each electrode of such conventional monitors is attached to an insulated wire that is routed to an amplifier to amplify the ECG signal. The patient has to take care not to pull on the wires connected to the electrode, because the electrode could be pulled off the skin.

Removing the electrode with its strong adhesive may be painful. Many electrodes also use a gel next to the skin to improve conductivity of connection of the metal electrode to the skin. Prolonged exposure to the gel can irritate the skin.

In ECG monitoring, there are several types of signal noise, called an "artifact." One kind of noise is caused by pulling on or rubbing over the wires which can deform the electrode. Noise can also be caused by the movement of clothing over the wires, movement of the electrode over the skin, noise generated by the electrical activities of muscles, and electromagnetic interference. Because of the various noise problems and loose wires, ECG signal quality is often compromised.

SUMMARY

Aspects of the present invention include a garment that includes a belt, having first and second end portion with closures at the end portions to wrap around a user's chest, a strap having a first end coupled to a portion of the belt with the strap having a second end, a pair of shoulder strap portions each shoulder strap portion having a first end coupled together at the second end of the strap and a second end and a back portion that joins the second ends of the pair of shoulder strap portions, with at least one of the belt, strap portions and back portion having an accommodation for carrying a sensor.

The following embodiments are within the scope of the invention.

The second end of the strap and the first ends of the pair of shoulder strap portions are unitary in construction. The second end of the strap and the first ends of the pair of shoulder strap portions are coupled together by fasteners. The back portion is unitary in construction with the pair of shoulder strap portions. The back portion is coupled to the pair of shoulder strap portions by a fastener. The back portion, the strap, and the pair of shoulder strap portions are comprised of synthetic rubbers based on polychloroprene material.

The accommodation for the sensor is disposed in the back portion of the garment, and the garment further comprises second and third accommodations disposed in each of strap portions and a fourth accommodation disposed in the belt of the garment. The accommodation is a pouch provided in the garment. The accommodation is a snap that mates with a corresponding snap on the sensor. The accommodation is provided in one of the belt, strap portions and back and the garment further includes at least one conductor to deliver a signal from the sensor to a processing circuit. The fasteners are selected from snaps, hook and loop fasteners. The accommodation is provided on a first one of the strap portions, in a portion of the strap portion that rests against a shoulder of a user. The sensor is permanently attached to the garment, for example with sewn stitches or with glue.

The garment further includes a sensor supported by the accommodation in the harness. The sensor includes a sensor membrane comprised of an electrically conductive, flexible material. The sensor membrane has a major surface thereof that is exposed to make contact with the skin of a subject, with the major, exposed surface that contacts the skin being a curved surface. The sensor membrane has a major surface thereof that is exposed to make contact with the skin of a subject, with the major, exposed surface that contacts the skin being a flat surface. The sensor membrane has the major surface covered with a conductive gel film. The sensor includes a snap member comprised of an electrically conductive material and is disposed in intimate contact with the backside of the sensing membrane to provide an electrical path for a signal from the sensing membrane. The garment further includes a sensor frame comprised of a firm, flexible material supporting the sensor membrane. The garment further includes a layer of material surrounding the sensor membrane to absorb sweat. The garment further includes a stiffener member to hold the sides and front of the belt forward of a user's body, when the belt is being put on and before it is fastened by the user.

Aspects of the present invention include a garment that includes a belt that is configured to be worn around a user's chest, the belt having a pair of ends with closures disposed at the pair of ends of the belt, at least one strap having a first end coupled to the belt and a second end, with at least one of the belt and strap having an accommodation for carrying a sensor and with portions of the garment that are on the skin side being comprised a high friction material.

The following embodiments are within the scope of the invention.

The garment further includes a back portion that connects to the belt and joins the second end of the strap. The first end of the strap is removably coupled to the belt. The strap couples between the belt and the back portion in a manner that the strap traverses the chest of a user. The strap couples between the belt and the back portion in a manner that the strap traverses the chest of a user and with the accommodation for carrying a sensor being a first accommodation disposed on the belt and the garment further comprising a second accommodation for carrying a second sensor, the second accommodation disposed on the strap in a region of the strap that contacts a shoulder of the user.

The sensor carried by the strap is attached in a region of the strap that contacts a shoulder of the user. The belt and the back portion are configured to secure the belt about the chest of the user. The garment further includes conductors attached to the sensors, the conductors being integrated into the garment. The garment further includes a sensor that is selected from an ECG sensor, motion sensor, body temperature sensor, respiration sensor or impedance plethysmography sensor. The sensor has an uneven surface having at least one of the features of nubs, bumps, ridges, grooves or conductive threads to maintain contact with the skin of a user when sliding over the surface of the skin and/or in the presence of hair, sweat, or uneven surfaces.

The shoulder strap is a first shoulder strap and the garment further includes a second shoulder strap, with the first and second shoulder straps coupled to the belt and with the shoulder straps configured to lie across shoulders of the user, in proximity to the sides of the neck of the user. The garment further includes a pair of brassiere cups and a second shoulder strap with the first and second shoulder straps coupled to the belt through the brassiere cups and with the shoulder straps configured to carry sensors. The garment is comprised of synthetic rubbers based on polychloroprene material. The garment further includes a stiffener to hold the sides and front of the belt forward of a user's body, when the belt is being put on and before it is fastened by the user.

One or more aspects of the present invention may provide one or more of the following advantages.

The wearable harness with integrated ECG sensors is suitable for long-term heart monitoring since the harness will likely be relatively comfortable and thus suitable to wear all day or while sleeping. The harness provides adequate contact of the sensors to the skin during exercise thus allowing the sensors to provide adequate ECG signal quality. Some embodiments can be worn comfortably by both men and women, whereas others are gender specific. The harness is thin, lightweight and inconspicuous.

The harness has integrated wiring thus avoiding entanglement or accidental removal of the wiring from the sensors. Thus, artifact suppression and patient comfort may be improved by integrating wiring into the harness, such that the connecting wires do not become tangled or pulled on by the sensors as in conventional Holter and event monitors. The wiring and sensors are shielded to reduce electromagnetic interference.

The sensors are made from comfortable materials that require little or no skin preparation or adhesive, unlike conventional ECG electrodes. The sensors may include high-friction materials to keep the sensors from sliding against the skin. The sensors are held tightly to the user's skin by tension from the harness, which is made out of a material (for example, Neoprene), that generally stays in place against the skin. Thin Neoprene as used in the harness acts like a second skin, stretching when the body stretches but not sliding over the surface of the skin, and keeping the sensors in a fixed position with respect to the body, instead of pulling the sensors and dragging them across the skin as some conventional approaches.

The harness holds the sensors at fixed and desirable positions on the body that are suitable for obtaining quality ECG signals. Because the harness tends to keep the sensors in place and the sensors themselves tend to resist sliding over the skin, and being located in areas with reduced muscle noise, the harness with integrated sensors achieves good quality ECG during exercise.

Aspects of the invention are directed to a wearable, thin and inconspicuous, harness with integrated ECG sensors and wiring for long-term heart monitoring, that is comfortable enough to wear all day and while sleeping. Some embodiments are suitable for both men and women, while other gender-specific embodiments are also described. By integrating, e.g., ECG sensors into the harness it is possible to eliminate adhesive between the sensor and the skin thus contributing to comfort for the user when using the sensors.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
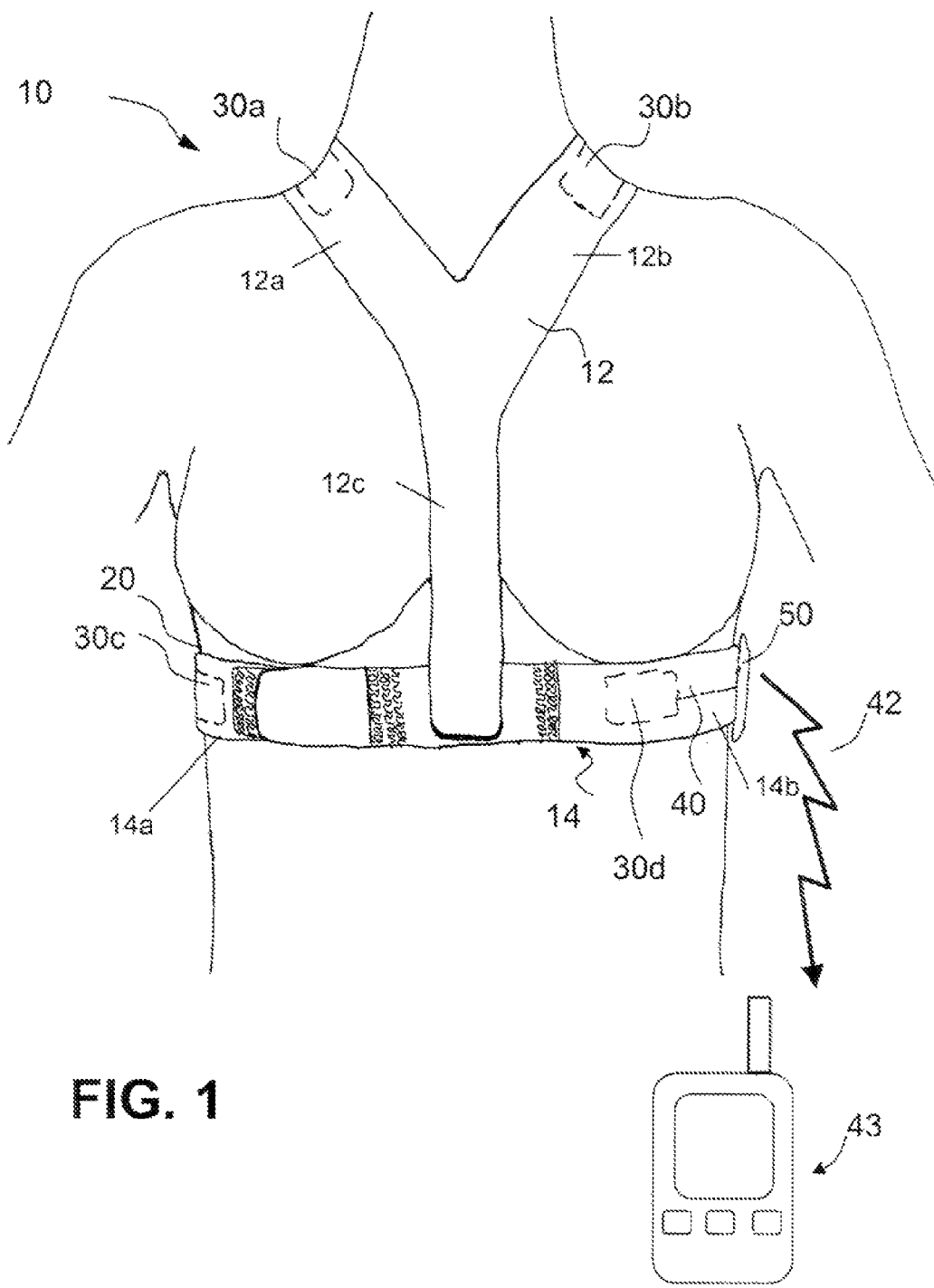
FIG. 1 is a front view of a harness on a female torso.
Figure 2:
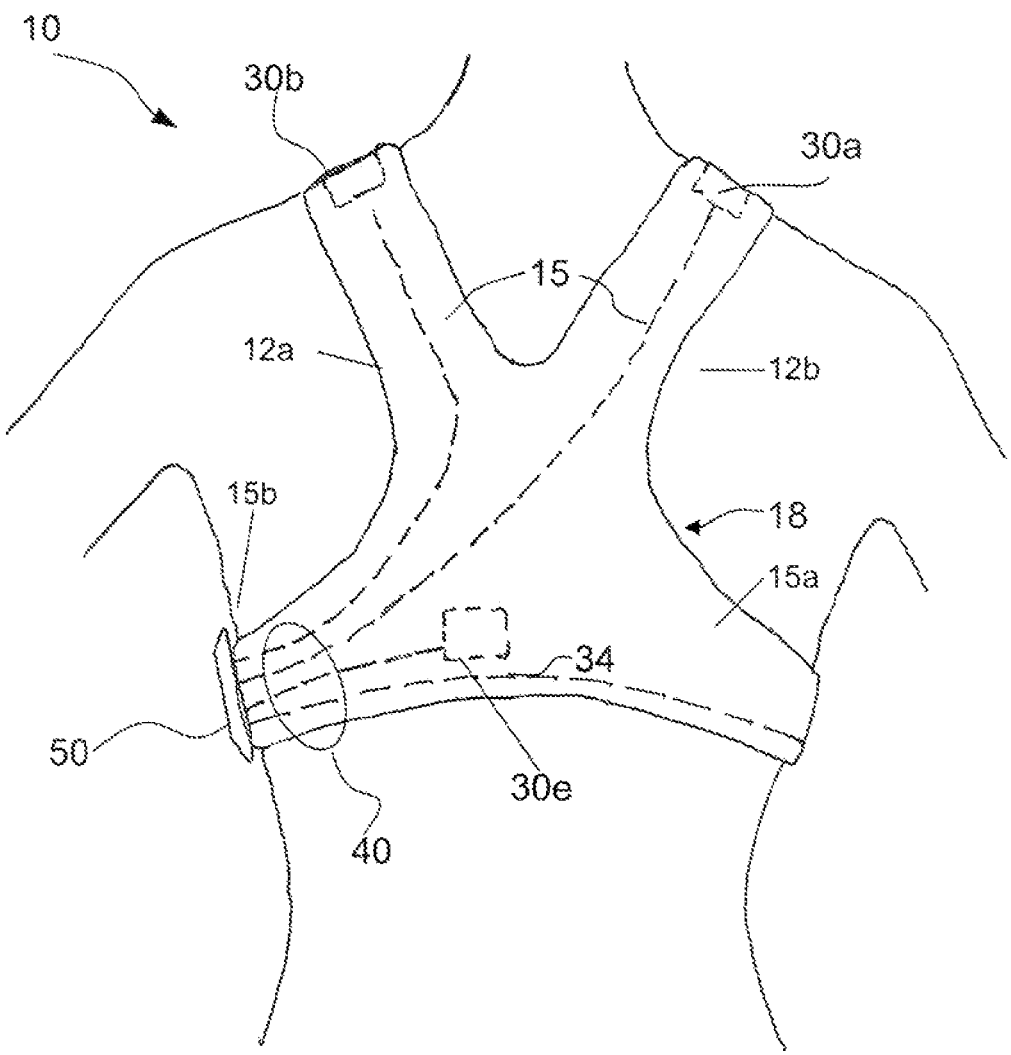
FIG. 2 is the back view of the harness of FIG. 1.

Referring to FIGS. 1 and 2, a harness 10 carrying physiological sensors is shown. The harness 10 is shown being worn on a female subject, but the harness can be comfortably worn by men also. The harness 10 is comprised of a thin, elastic material. Exemplary materials include synthetic materials such as synthetic rubbers such as Neoprene® (DuPont Performance Elastomers), other synthetic rubbers based on polychloroprene (polymer form of Chloroprene). Other materials could be used. Ideally, the material is one that can be worn comfortably next to the skin of the subject and has some resistance to movement or sliding against the skin of the subject.

Figure 4:
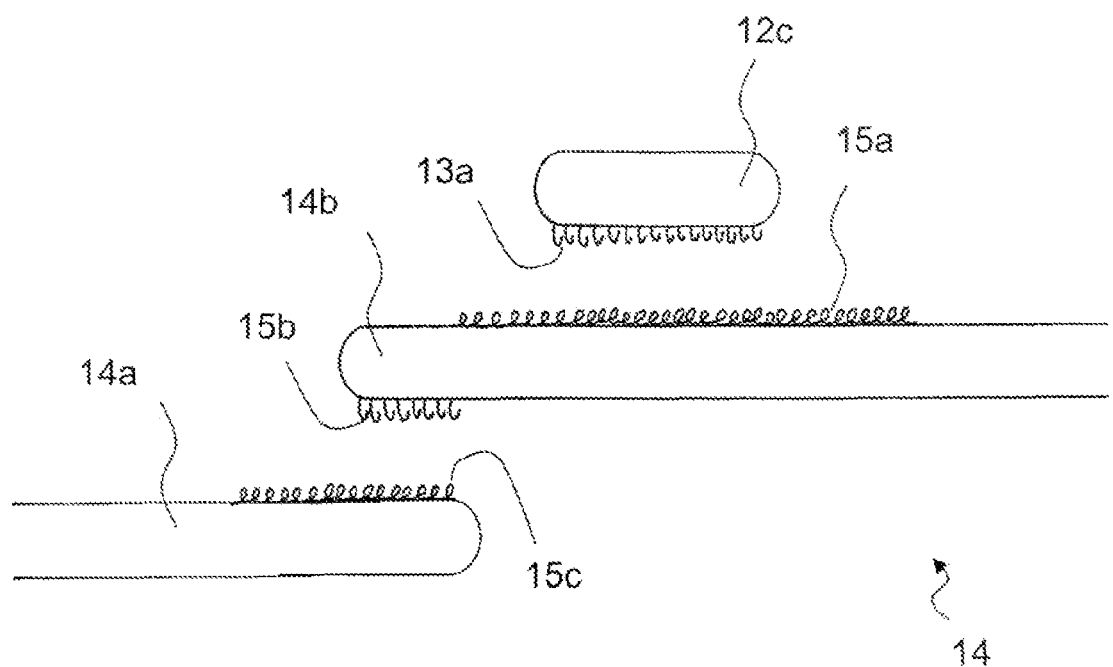
FIG. 4 is a cross-sectional view of a portion of FIG. 1 showing details of connection of the harness of FIG. 1.

The harness 10 includes a generally "Y" shaped front portion 12 (FIG. 1) having a pair of strap portions 12a, 12b that rest over shoulders of the subject and meet at a vertical portion 12c below the breast forming a generally "Y" shape in the front of the harness 10. The strap portions 12a, 12b extend over the shoulders and meet at a broad region 18 that rests against the back of the subject, as shown in FIG. 2. The harness 10 also has a chest belt portion 14 comprised of two straps 14a, 14b each of which emanates from the broad region 18 in the back and are disposed around the torso. The straps 14a, 14b overlap each other in the front under the breast and are secured together via a hook and loop fastener configuration such as Velcro® (Velcro, Inc. Nashua N.H.), as depicted in FIG. 4 below.

The shoulder straps 12a, 12b hold or carry shoulder sensors 30a and 30b that are placed close to the neck of the subject. The sensors are carried by or in accommodations for the sensors, which can be attachment mechanisms, pockets and so forth as will be discussed below. The straps 12a, 12b surround the neck, a placement that minimizes stretch in the shoulder straps 12a, 12b. If a strap stretches too far, the strap can pull on the sensor, causing noise in the electrical potential sensed by the sensor from the skin.

This configuration of the harness 10 allows for comfortable placement of a plurality of sensors. As illustrated in FIGS. 1 and 2, five sensors, 30a-30e are supported against the skin of the subject and disposed to place sensors 30a-30e at places on the body that are useful for ECG. Described below are examples of particular placement locations for the sensors for ECG monitoring. Sensors 30a-30e are connected by wires 40 to an electronics module 50. The wires 40 are integrated into the harness material.

The components, e.g., straps 12a, 12b, vertical member 12c, chest band straps 14a, 14b, and broad region 18 of the harness can be constructed as individual pieces that are secured together, either being sown, solvent welded, using a hook and loop fastener configuration and so forth, depending on material and other construction considerations. Alternatively, the harness 10 can be molded or otherwise constructed in a more unitary manner, as shown in FIGS. 1 and 2.

The harness 10 can be sized to fit men or women, as well as children. The harness 10 can come in various sizes or component construction can be employed to fit various components of the harness to the individual using various fastener schemes as mentioned above.

The shoulder straps 12a and 12b together with the vertical strap 12c provide a Y-shaped harness. The shoulder sensors 30a and 30b are placed close to the neck on straps that surround the neck. This placement minimizes stretch in the shoulder straps. If a strap stretches too much, it can pull on the sensor, imparting noise in the electronic signal provided from the sensor. The sensors 30a and 30b are placed near the top of the shoulder where they are pulled onto the skin by the shoulder straps 12a, 12b, regardless of the position of the user.

The harness 10 comfortably attaches to the user around the chest with the chest band 14 positioned just under the pectoral muscles in the front. The chest band 14 can be adjusted to be snug around the chest with an adjustable closure, for example, the hook and loop type of fastener mentioned above.

The harness also carries an electronics module 50 that can wireless transmit signals from the sensors to a nearby computer, PDA or wireless phone. A PDA 43, as shown, may be carried by the person wearing the harness 10.

Figure 3:
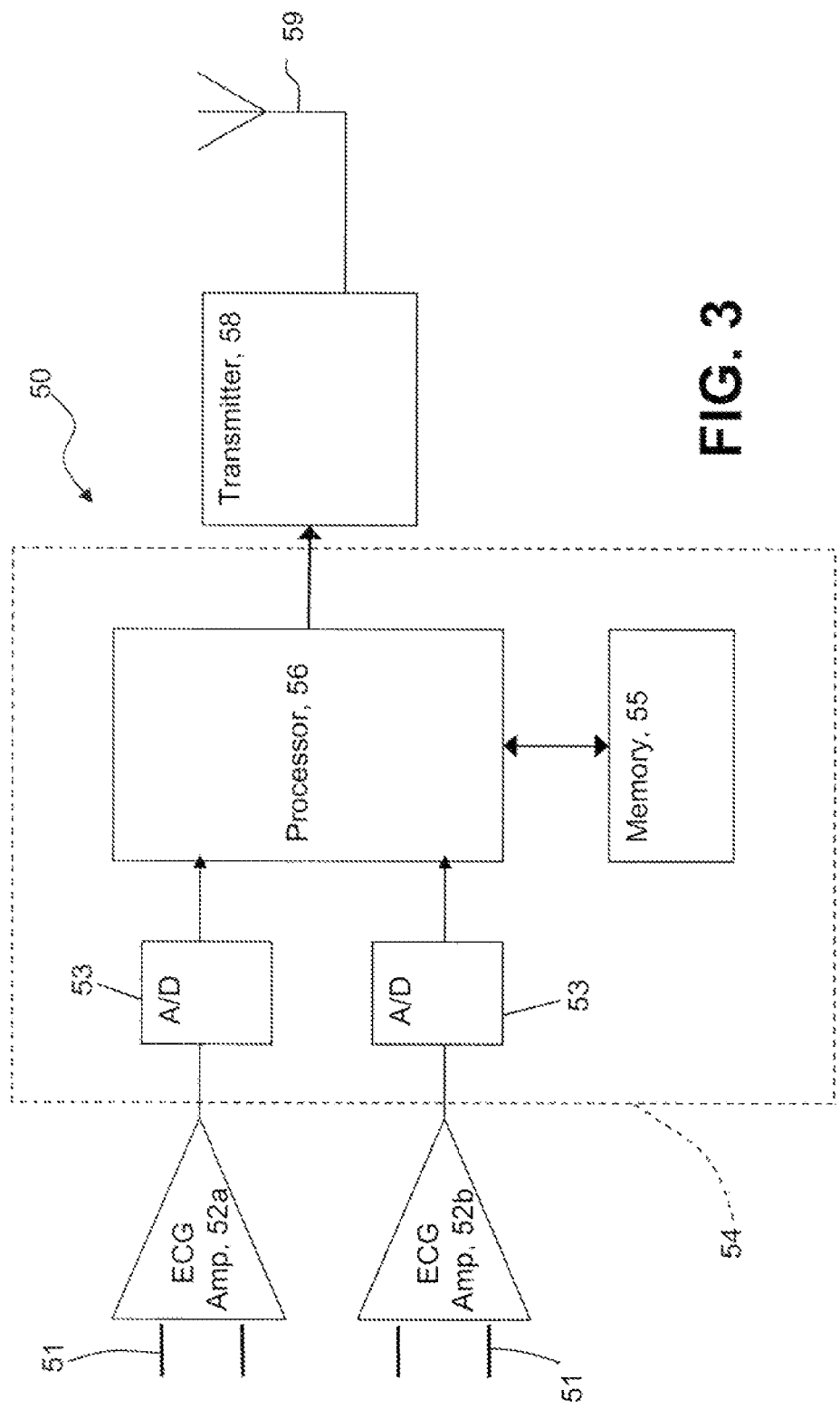
FIG. 3 is a block diagram of a typical electronics module.

Referring to FIG. 3, the electronics module 50 typically includes input connectors 51 that are connected to signal amplifiers 52a-52b. Typically, two sensors which are in positions on the subject to pick up a differential signal across the subject's heart are input to each differential amplifier. For example in FIG. 3, four individual sensors (for example 30a-30d) could be connected to the four inputs 51. Any number of sensors and amplifiers could be used.

The two amplifiers receive signals from two sensors via an integrated wiring system. The signals from the sensors are amplified, and the amplified signals from these amplifiers are fed into pre-processing circuitry 54 that prepares the signals for transmission and subsequent processing. The pre-processing circuitry 54 can include one or more A/D converters 53 to digitize the signals from the amplifiers, and may optionally include filters to filter the signals or perform signal processing and identification of physiological conditions. The pre-processing circuitry 54 includes a memory 55 (and/or storage) and a processor 56 to implement filtering and processing functions to provide intermediate results and to store information before transmission. Other circuitry is not shown for instance, timing, interface circuitry and so forth.

The pre-processing circuitry 54 couples the pre-processed signals to a transmitter 58 and antenna 59 that transmits the signal to a base station 43 (FIG. 1). The signal may be transmitted using, for example, Zigbee or Bluetooth protocols, to a base station that can be a computer, PDA (as in FIG. 1) or wireless phone and so forth. An example of an electronics module 50 is the Alive heart monitor by Alive Technologies Pty. Ltd., (International publication No. WO2005/048830). The Alive heart monitor receives an ECG signal from 2 sensors, amplifies the signals, digitizes the signals, and transmits the signals, via the Bluetooth protocol.

Typically, the electronics module 50 is enclosed in a case that can be removed from the harness 10 for washing, and reattached using connectors 51. An alternative is to enclose the electronics module 50 and its battery in a waterproof container and permanently attach the electronics module 50 to the harness 10.

In some configurations, the sensors are coupled to an analog multiplexer and the output of the multiplexer is coupled to an amplifier. In that configuration a circuit (not shown) selects which sensor to couple through the analog multiplexer.

There are several scenarios for how the sensor harness might be used including, for example, that signals might be analyzed by the PDA/phone and transmitted to a monitoring center for review by a physician. Alternatively, instead of attaching an electronics module 50, the harness could be hard-wired to a hospital ECG monitoring machine, and used to comfortably monitor ECG on a sleeping patient, for example.

Referring to FIG. 4, the chest band 14 (FIG. 1) is secured around the chest of the subject and the vertical member 12c is attached to the chest band 14, as shown. A portion of the underside of the vertical member 12c is covered with hook members, e.g., Velcro® hooks 13a, which mate with Velcro® loops 15a on a top layer of chest strap 14b. The underside of chest strap 14b is covered with Velcro® hooks 15b that mate with the loops 15c on the chest strap 14a. Other fastening mechanisms are possible, such as snaps, zippers, hooks, etc.

The "Y-configuration" 10 of the harness is acceptable to both men and women and provides specific sensor locations to sense voltages for ECG monitoring. However, there are other strap arrangements that embody the basic idea of the harness, that is, a thin and comfortable EGG sensor garment with chest and shoulder straps that can be worn by men and women.

The shoulder straps 12a, 12b of the harness 10 hold or carry shoulder sensors 30 and 31 close to the neck of the subject. By surrounding the neck that placement of the shoulder straps minimizes stretch in the shoulder straps and concomitant movement of the sensors. Other arrangements are possible.

Figure 5:
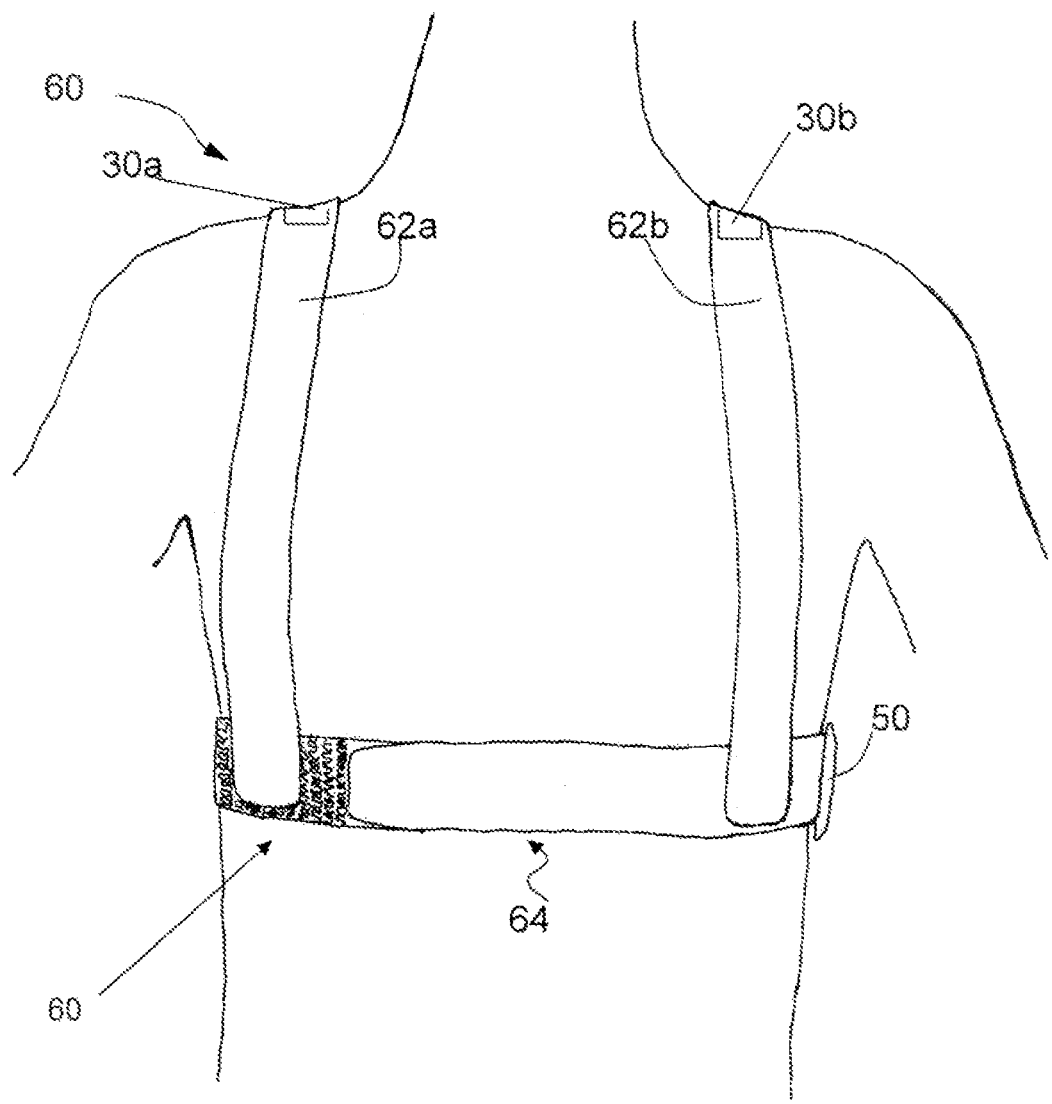
FIG. 5 is a front view of an alternative harness.

Referring now to FIG. 5, an alternative suspender harness 60 includes a pair of generally vertical shoulder straps 62a, 62b that are attached to and hold a chest belt 64 in position in a similar manner as would a pair of suspenders hold a pair of pants. When worn by a subject, the shoulder straps 62a, 62b are disposed towards the middle of the shoulders, as compared to the Y-harness 10. The shoulder straps 62a, 62b may tend to stretch more when the arm is lifted. Sensors 30a-30b are placed near the top of the shoulder straps 62a, 62b where they are pulled onto the skin by the shoulder straps 62a, 62b.

The shoulder straps 62a, 62b connect to the chest belt 64 towards the sides of the chest belt (not the middle as in the Y model). The harness 60 can also be worn on a woman because the shoulder straps 62a, 62b are towards the sides of the chest.

In the harness 60, e.g., five sensors (30a and 30b being shown) can be provided in the same general locations as in the Y harness 10. In addition the harness 60 also has a back region that can be similar to 16 in FIG. 1 or they can be connected directly to the chest belt 64. However, because the shoulder straps 62a, 62b are not as close to the neck, as in the Y harness 10, the shoulder sensors 30a, 30b may be prone to more electrical noise in the sensed signal due to muscle movements and sensor movement from the straps being stretched than would likely occur with the Y harness 10. While the harness 60 may be less desirable to use when performing vigorous arm movements, it may be more comfortable to put on because it does not involve pulling the garment over the head and it is not tight around the neck as the harness 10.

Figure 6:
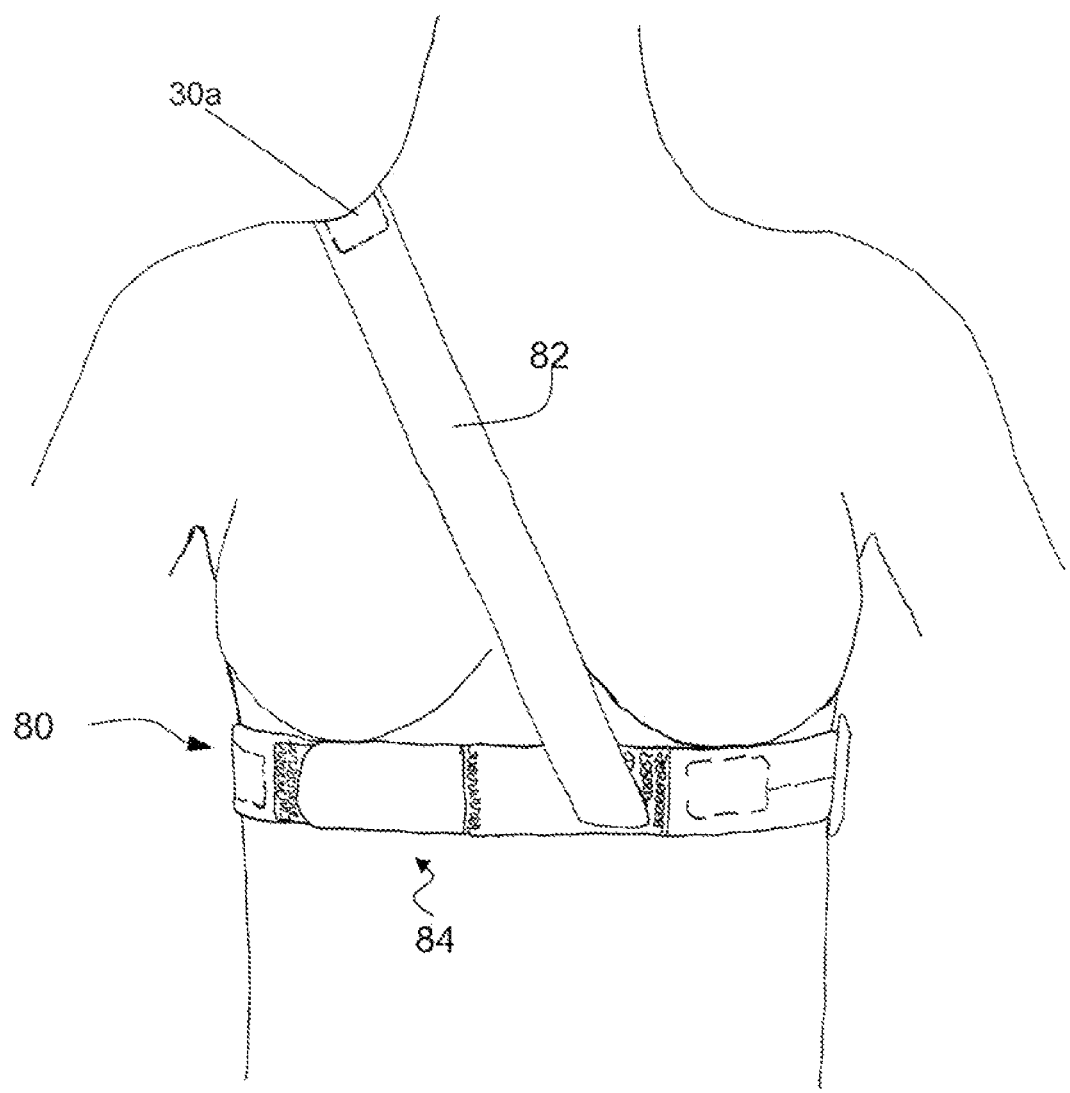
FIG. 6 is a front view of another alternative harness.

Referring to FIG. 6, another variation of the sensor harness is the single shoulder strap embodiment 80. The single shoulder strap 80 has one shoulder strap 82 with a sensor 30a that drapes over one of the shoulders of the subject, e.g., the right shoulder as shown and is attached to the chest belt 84 on the opposing side, e.g., the left side of the chest belt 84.

The chest belt 84 is in the same position as the other designs, under the pectoral muscles. The shoulder strap crosses between the breasts and so is comfortable for women.

The Y-shaped design 10, the suspender harness 60 and the single strap design 80 can all have the garment cut or formed in a style acceptable to both genders, as well as children. Generally, women may accept clothing with some prototypically masculine cues, while men are less willing to accept feminine features. For example, very thin shoulder straps such as those typically found on a bra might be seen as feminine. For this reason, the harness can have shoulder straps 15 (FIG. 2) that are at least, e.g., one inch in width. Other widths are possible. The shoulder straps are also wide to help distribute the pressure from the tight harness. The harness 10 features a broad back area 18 that comes up high towards the neck, a feature often encountered with both male chest harnesses and some female sports bras, and so would likely be acceptable to both men and women.

Figure 7:
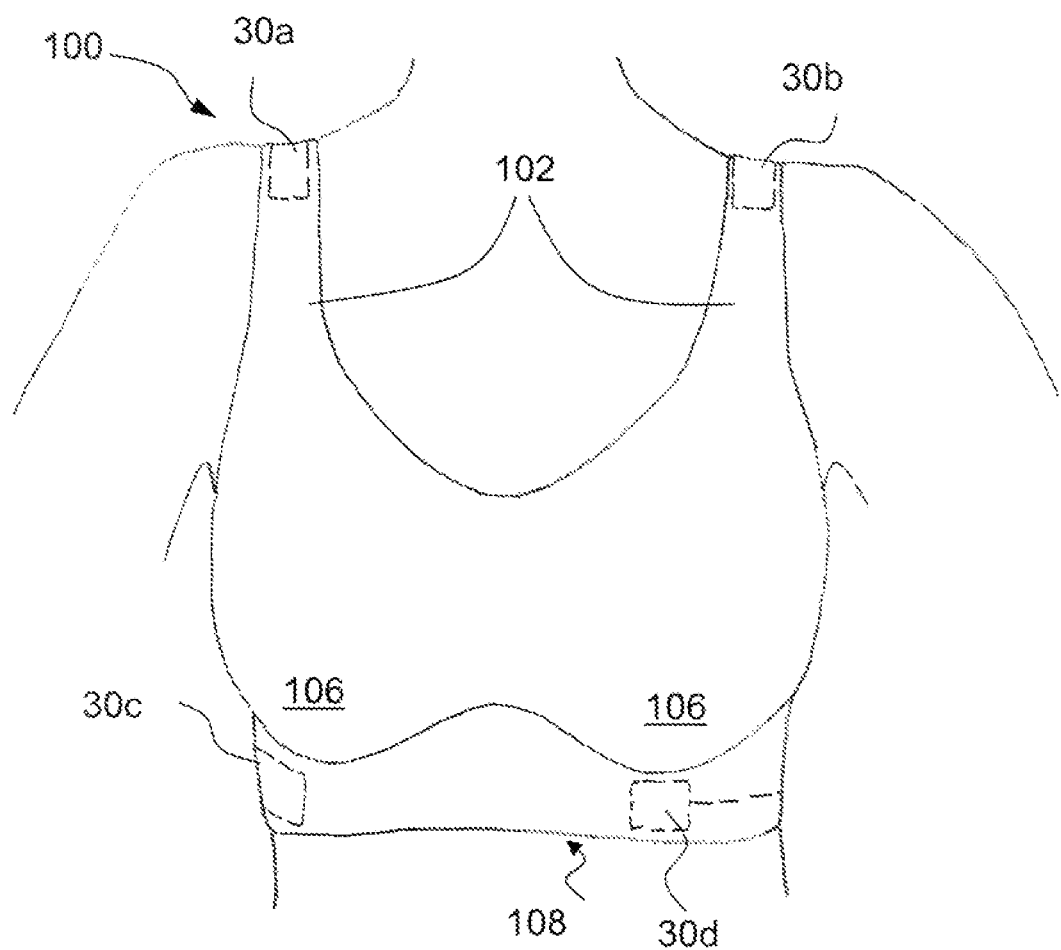
FIG. 7 is a front view of an example of a harness configured as a brassiere.

Referring now to FIG. 7, an alternative embodiment 100 particularly suited for women is shown. This embodiment is as a bra or brassiere 100 having a pair of straps 102 carrying sensors 30a, 30b and a pair of bra cups 106. The straps 102 are coupled to the pair of cups 106 at one end and at the other end are coupled to the back of the bra (not shown, but similar to 18 of FIG. 2 or alternatively of more conventional brassiere construction). A belt 108 is fitted or coupled to or is an extension of the underside of the cups of the bra 100, and holds sensors 30c, 30d flat against the chest just under the breasts. A sensor (not shown) can be provided at the back portion of the harness 100.

Figure 8:
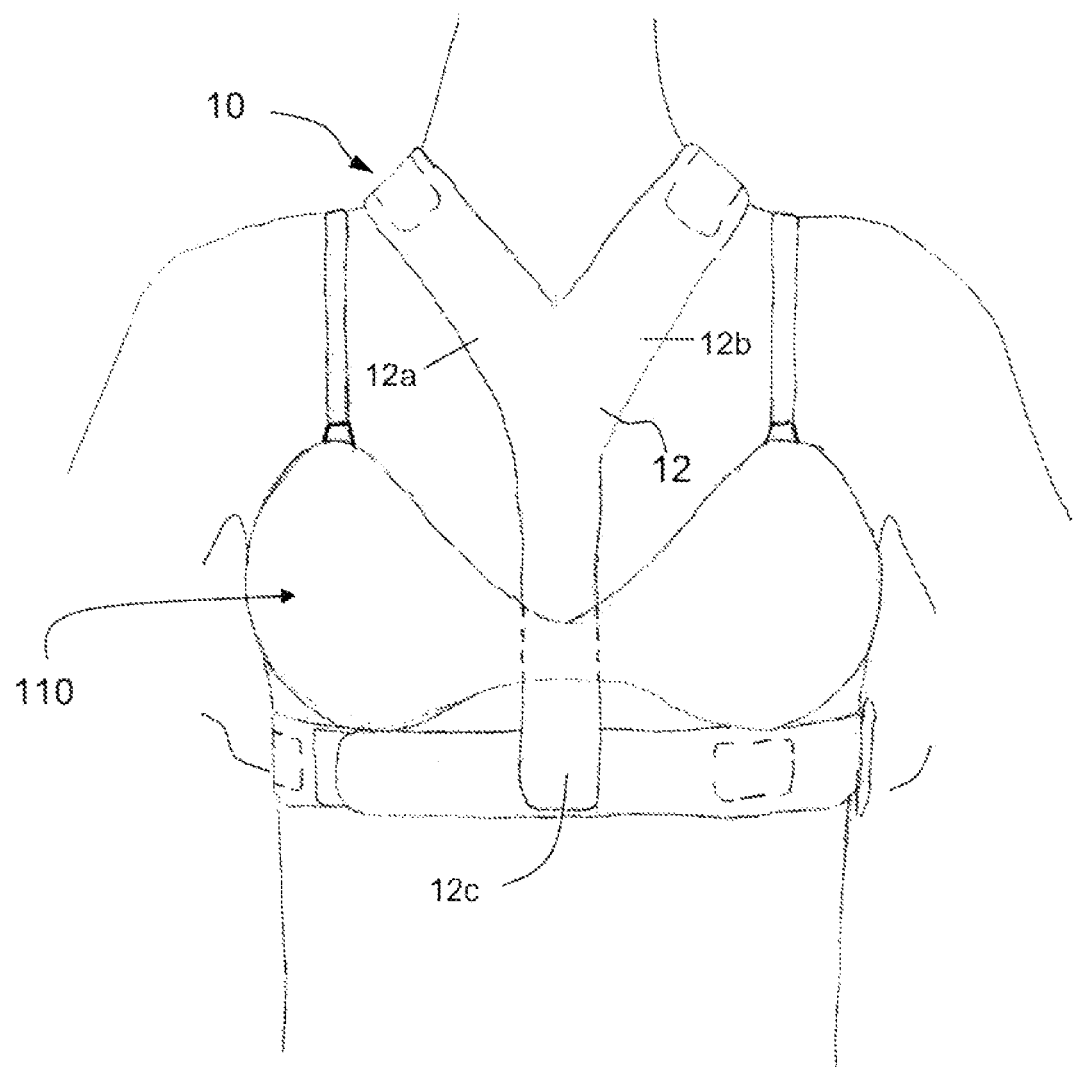
FIG. 8 is a front view of a female torso wearing the harness of FIG. 1 with a brassiere.

The variations of the sensor harness described above may work on adult or child body types (thin or fat, large or small), when suitably sized. The harness (Y shaped, single strap, and suspenders) can all be worn comfortably with a conventional bra 110, as illustrated in FIG. 8. Because the strap 12a, 12b material can be made thin (e.g., 3 mm or less), the harness 10 may comfortably and easily fit under most bras in the front, where the center of the bra lies on top of the bottom of the Y strap 12c. Because the shoulder straps 12 of the harness are close to the neck, they do not, in general, overlap the bra shoulder straps.

The harness approach 10, 60 and 80 or the variation 100 can provide good quality contact with the skin of the patient for good quality ECG voltage signal sensing during rest, exercise and sleep. The harness 10 provides tension to hold the sensors tightly against the body during rest and exercise. During rest, the harness 10 provides tension and positions the sensors in place against the body. During exercise, some sweat may build up under the sensors, which is beneficial to the function of many types of sensors, providing reduced resistance between the sensor and the skin.

The harness 10, 60 and 80 or the variation 100 can be made from a material that is thin, strong, and somewhat elastic, making it comfortable to wear. Ideally, the material used would be comfortable against the skin, when first put on, when worn and even when sweating. Ideally, the material will act like a "second skin" by stretching when the skin stretches, but not sliding over the surface of the skin. The material can be washable. The material can be a synthetic rubber such as Neoprene® (DuPont). Neoprene has a tendency to stay in the place where it has been put on the skin. When the user sweats, Neoprene retains a non-slip quality to some degree. However, large amounts of sweat between skin and Neoprene may allow the Neoprene to slip against the skin. For high-sweat applications, the harness material can be manufactured with holes to allow sweat to evaporate more quickly. The Neoprene material can have a thickness of 1.5 mm or so, although a double layer might be preferable, which would be approximately 3 mm or so in thickness.

Referring back to FIGS. 1 and 2, several specific sensor locations are shown for the Y harness 10. The Y harness 10 has two shoulder sensors 30a and 30b, two sensors on the chest band 30c and 30d, and a sensor on the back 30d. For the Y harness 10, the shoulder sensors 30a and 30b are placed close to the neck, on a part of the shoulder that does not experience much movement, in order to reduce the amount of muscle movement and thus noise imparted to signals sensed by the sensors 30a, 30b. The shoulder sensors 30a, 30b can be placed on top on the shoulders or on the clavicles. The location of the harness on the body (all models) performs very well at keeping the sensors in place, because the harness does not cover much skin area and lies in places that do not experience much skin movement or stretching.

The sensor 30d is located in the chest band on the subject's left side, in the vicinity of ECG electrode locations V4 and V5, very close to the heart. Sensor 30c, located on the subject's right side, is near the V6R position, whereas sensor 30e is positioned in the middle of the subject's back. These five sensor locations can be used in a variety of ECG lead configurations. A differential or bipolar ECG lead from sensor 30a to 30b produces a signal similar to the standard ECG lead I; sensor 30b to 30d is similar to Lead II; sensor 30a to 30d is similar to Lead III. Sensor 30c could be used as a reference electrode, like conventional electrode location RL. Lead II is well-known as the best lead for detecting P waves in the ECG, which are useful for diagnosing particular heart conditions like atrial fibrillation.

Wearable sensors may not provide as reliable a signal as conventional ECG electrodes with adhesive. Therefore, it may be desirable to set up 2 or 3 independent bipolar leads, such as a lead from sensor 30b to 30d (Lead II), and another lead from sensor 30a to 30c, for example. With independent leads, even if one sensor loses contact and become unusable, the other lead still provides a signal for an ECG. The back sensor 30e (see FIG. 2) is well-positioned for picking up ST segment changes in the ECG, which can indicate ischemia.

For each user, the harness will place the sensors in the same position every time the harness is put on, because its shape tends to put it on the same place on the body. Therefore, sensors remain in substantially the same position, and changes in ECG can be measured over time, which is useful for detecting conditions like the onset of ischemia, in which changes in ECG morphology occur over a period of time.

Figure 9:
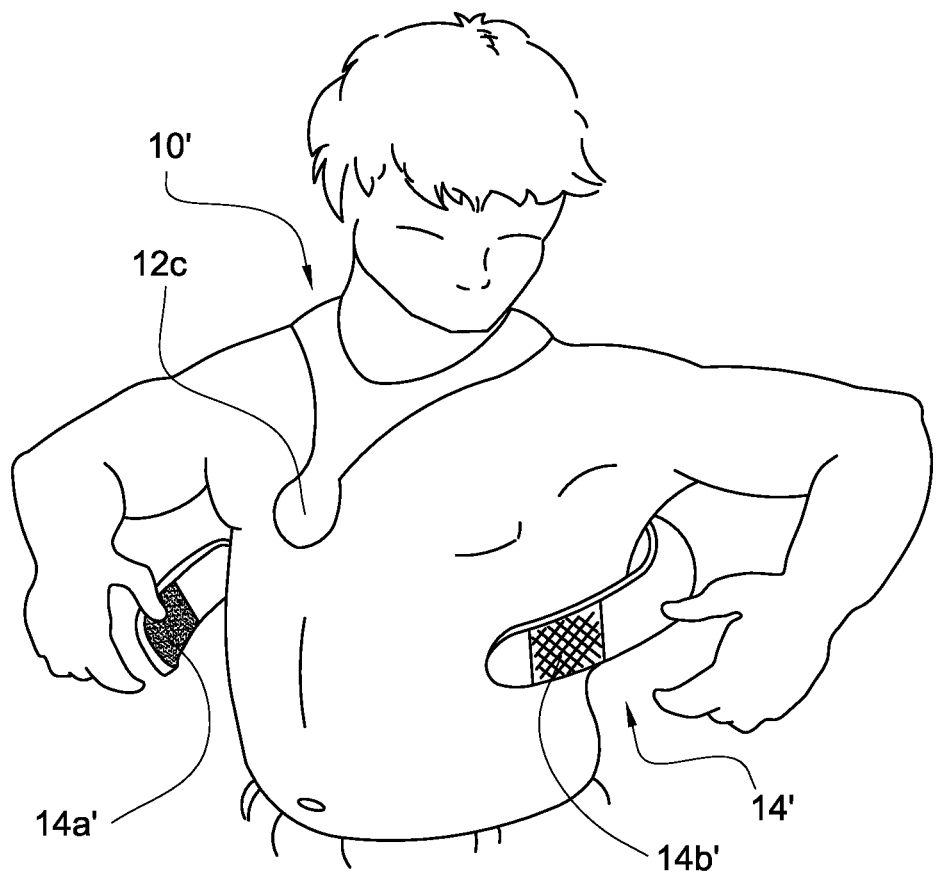
FIG. 9 is a diagram depicting movements to secure the harness of FIG. 1.

Referring to FIG. 9, another alternative 10' to the harness 10 (FIG. 1) has a stiff but flexible chest strap 14' that when put on, holds its shape to present the side straps 14a' and 14b' in a position forward of the body so the user can easily grasp them. The chest strap is flexible enough for the user to pull the strap tightly around the chest and secure the chest strap 14' by touching the ends of the side straps together, which are held fast by, for example, Velcro. The bottom of the Y, 12c, is pulled down and attached to the chest strap 14'. To take the harness off, the process is reversed. Any wearable physiological monitor should be easy to put on and take off, because many of the people who need monitoring for cardiac diseases are sick or elderly and have limited mobility.

Figure 10:
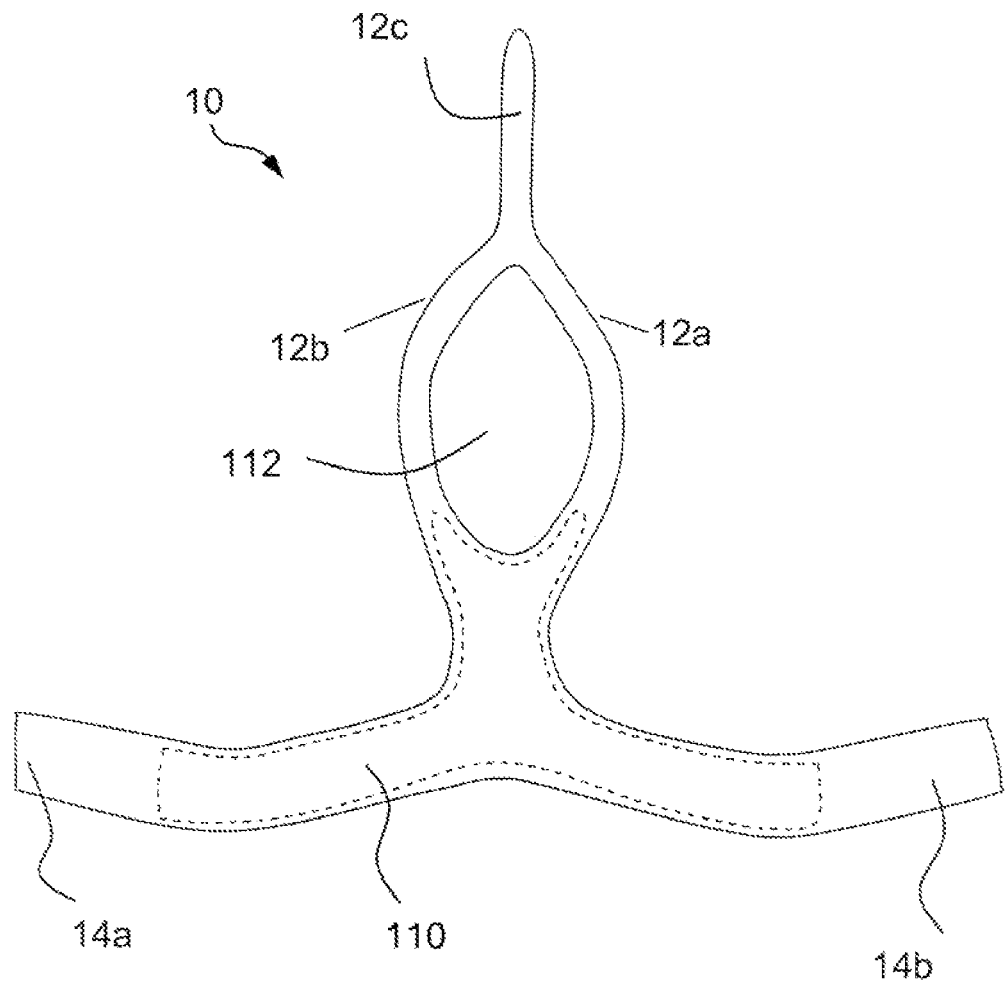
FIG. 10 is a plan view of the harness of FIG. 1 having a stiffener member, the harness laid-out on a surface.

Referring now to FIG. 10, one way to provide a harness with the desired affect of presenting the sides 14a' and 14b' in front of the body is to attach or embed a stiff plastic material 110 to the harness, to maintain curvature in the harness as shown in FIG. 9. The stiffener 110 can be placed in between two layers of Neoprene that make up the material of the harness 10. The stiffener 110 is curved in a U shape (not shown, but as would be viewed into the page) causing the chest belt ends 14a' and 14b' to be oriented as shown in FIG. 9.

When the Y harness 10 of FIGS. 1 2, and 9 is laid on a flat surface, it looks as in FIG. 10, with the end of vertical portion 12c at the top of the figure, and the left and right ends of the chest strap 14a and 14b at the left and right ends of the figure. The shoulder straps 12a, 12b form a neck-hole 112. The Y harness 10 is put on by first placing the head-hole 112 over the head, with the vertical portion 12c in front.

The harness 10, 10', 60, and 80 or the variation 100 are configured to place ECG sensors at physiologically interesting and useful places on the subject. However, the harness can hold other types of sensors, some of which can be of use in interpreting or processing the ECG signal. The harness could incorporate motion sensors to detect motion that can be used, for example, to invalidate portions of time in the ECG signal from a nearby ECG sensor when a large amount of motion is detected and the signal was thus presumably corrupted by noise caused by the motion of the sensors relative to the skin. A respiration sensor can be provided by placing a sensor in the chest band 11 which can measure stretch of the chest band. This signal can be used in ECG processing, for example to remove respiration artifact. ECG sensors can be used in conjunction with impedance plethysmography sensors to measure cardiac output. Sensors to measure surface skin temperature may add to the overall measure of user health.

Sensors could be permanently integrated into the harness 10, 10', 60, and 80 or the variation 100. Several wearable sensor materials, discussed in more detail below, are robust enough to be washed along with the harness 10, 10', 60, and 80 or the variation 100. Another option is to have some portion or all of the sensors removable and/or disposable. This would allow different types of sensors to be used for different activities. For example, exercise generates significantly more sweat than sedentary activity, so different sensor designs could be used depending on the anticipated level of perspiration.

Figure 11:
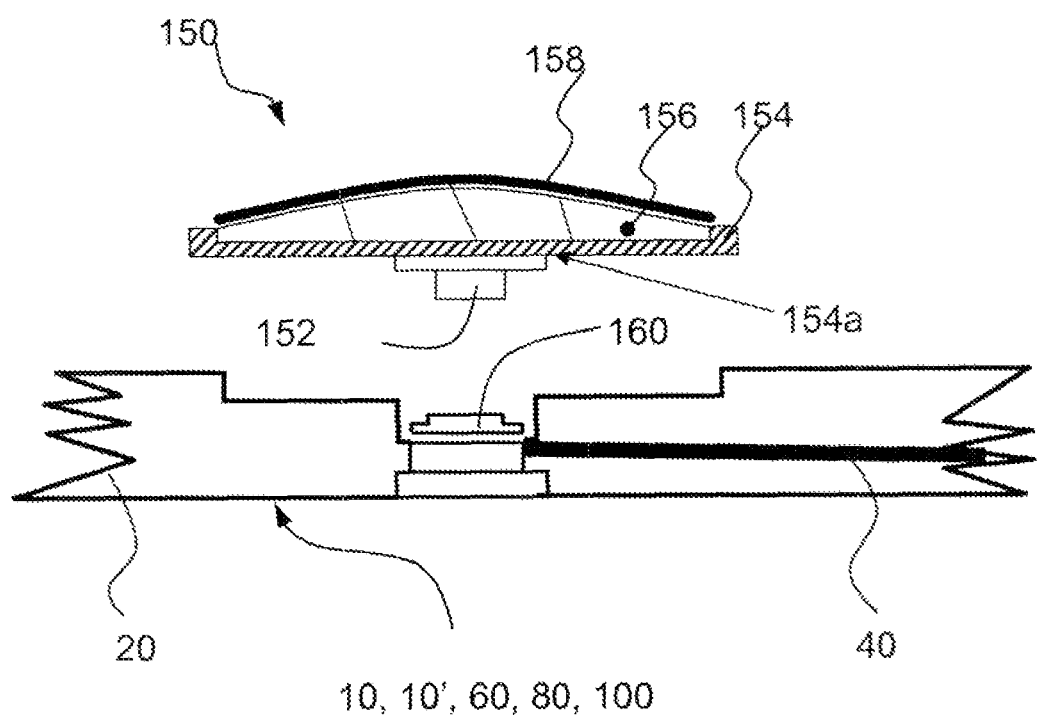
FIG. 11 is a cross-sectional view of a removable sensor.

Referring to FIG. 11, a removable sensor 150 for sensing voltages from the skin to provide a signal for ECG monitoring is shown in cross section, disposed in a portion of a harness, e.g., harness 10 (FIG. 1). The removable sensor 150 has a snap 152. The snap 152 is attached to a sensor frame or housing 154 that is comprised of a firm but flexible material (e.g., rubber). The housing 154 is used to support a more flimsy, e.g. compliant lower Young's modulus material that provides a sensor membrane 156. The sensing membrane 156 is comprised of an electrically conductive and flexible material, e.g., a conductive rubber or conductive silicone and is disposed inside the housing 154 and has a major surface thereof that is exposed so that the sensing membrane 156 can make contact with the skin. The sensing membrane 156 can be flat or can be curved as shown, to insure secure and adequate contact with the skin.

The sensing membrane 156 may be temporarily covered with a conductive gel or a hydrogel film 158. A thin hydrogel film could be cut to size, and would provide excellent skin conduction to a wearable sensor material such as conductive silicone. Hydrogel, however, is not very durable and so the hydrogel might be used for, e.g., a day and then discarded and replaced.

The snap 152 is comprised of an electrically conductive material, e.g., a metal, conductive plastic, or hard conductive rubber and is disposed in intimate contact with the backside of the sensing membrane 156 to provide an electrical path for a signal from the sensing membrane 156 to a mating snap 160 on the harness. This contact can be provided either by having the membrane in intimate contact with a back portion 154a of housing 154 or though an aperture (not shown) in the back portion 154 to allow the snap 152 to be directly connected to the membrane.

The harness in this example would have an accommodation for the sensor 150. Here the accommodation is a mating snap 160. The removable sensor 150 thus attaches to the harness by mating the snap 152 on the sensor 150 with the corresponding mating snap 160 on the harness. In this configuration a wire 40 would be coupled to the mating snap 160 to carry the electrical signal to the electrical circuitry (FIG. 3). The garment's snap 160 attaches to the harness by being disposed through an aperture in the material and crimped to surrounding material of the harness to hold the snap 160 to the harness.

Figure 12:
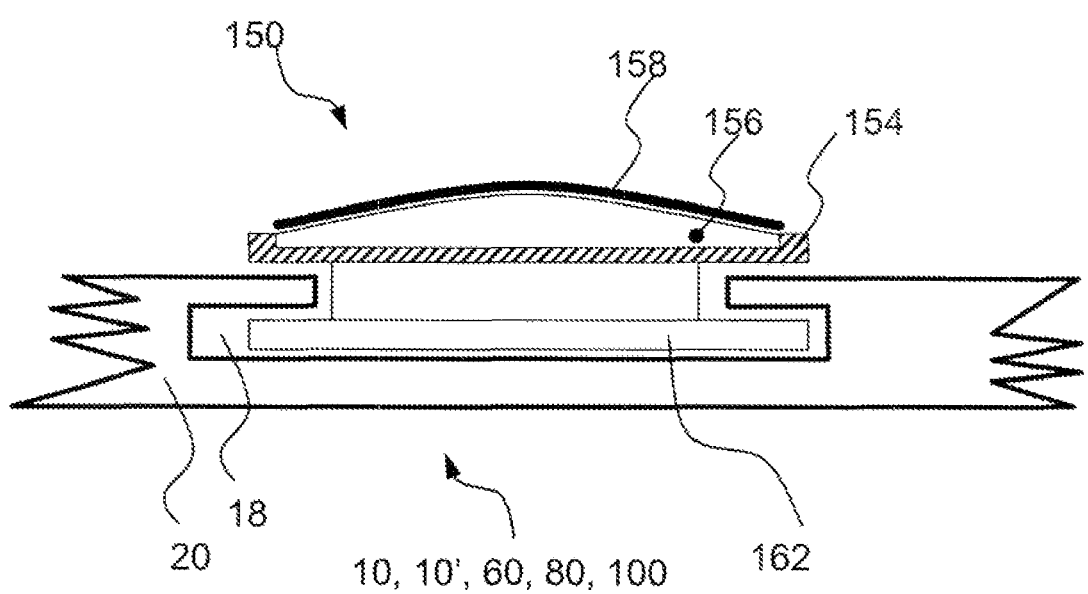
FIG. 12 is a cross-sectional view of an alternative removable sensor.

Referring to FIG. 12, another example of a removably attachable sensor for use with the harnesses or other garments is shown. This sensor is configured to fit into an accommodation that is a pocket 18 or opening in the harness or other types of garments. The pocket could be formed by fabricating the garment from two layers of material 20. The sensor 150 is shaped so that the bottom of the sensor 162 fits in the pocket 18. The sensor 150 may fit snugly in the pocket 18, in which ease the harness would provide the function of holding the sensor in place, as previously discussed. Alternatively, the sensor 150 could fit loosely in the pocket 18, allowing the garment or harness to move and stretch. The face of the sensor 150 would preferably be a high friction material to hold the sensor against the skin.

There are sensors that do not need direct skin contact, such as capacitively coupled sensors for measuring ECG. These types of sensors could slip into a pocket in the garment and would not need to be in direct contact with the skin of the subject.

Thus, sensor attachment could be a permanent attachment to the garment or could be removable. Parts or all of a removable sensor could be disposable (e.g. the hydrogel membrane). Other examples of mechanisms for removable sensors include conductive Velcro or other hook and loop type fastener mechanisms, a buttonhole in garment (with the sensor configured as a round button-like object), and sensor prongs that fit in holes in the garment.

The ECG sensors can be provided with electrodes comprised of metal such as a conventional silver/silver chloride compound. While this metal material could be used, the metal material is somewhat inflexible, does not naturally stick to the skin, and can become slippery in the presence of perspiration. Other materials can be used such as conductive silicone, a wearable material commonly used for shock therapy electrodes, or conductive rubber provided by adding conductive, skin-friendly materials such as silver, gold or carbon to liquid rubber and molding the composition into the desired shape of a sensor. Other conductive materials can be used such as a conductive fabric provided by weaving fine threads of silver together with conventional fabric threads; or coating fabric threads with metal. Hydrogels can be used as a thin layer between any of these wearable sensor materials and the skin as previously mentioned. These materials are suitable for sensing EGG signals from the skin without any skin preparation. The shape of the sensor can help maintain contact with the skin.

Figure 13A:
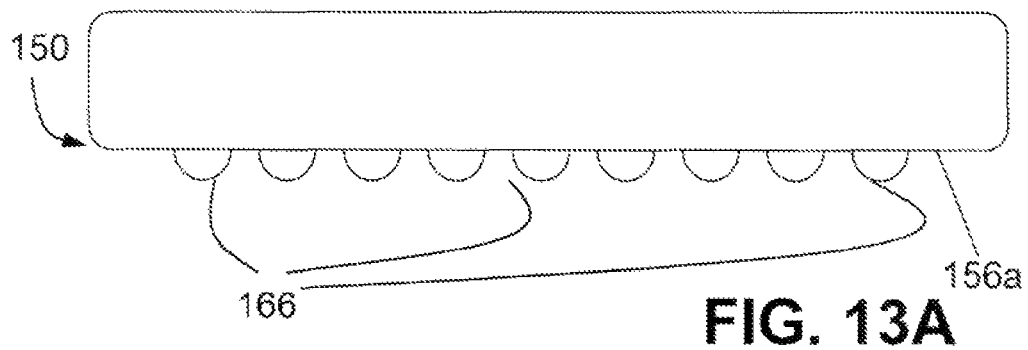
FIGS. 13A-13D are cross-sectional views showing possible surface preparation for sensor membranes.

Referring now to FIGS. 11 and 12, a smooth rounded sensor that would gently push against the skin to make contact is shown. FIGS. 13A-13D shows cross sections of sensor faces showing different textures. In FIG. 13A, the sensor 150 has a sensor face 156a with nubs or bumps 166 shaped like gumdrops on the surface of the sensor that touches the skin. This configuration of the surface would be suitable for working around body hair, as the nubs would have a good chance of pressing in between the hairs to reach the skin. Excessive sweat could also be channeled between the nubs 166.

Figure 13B:
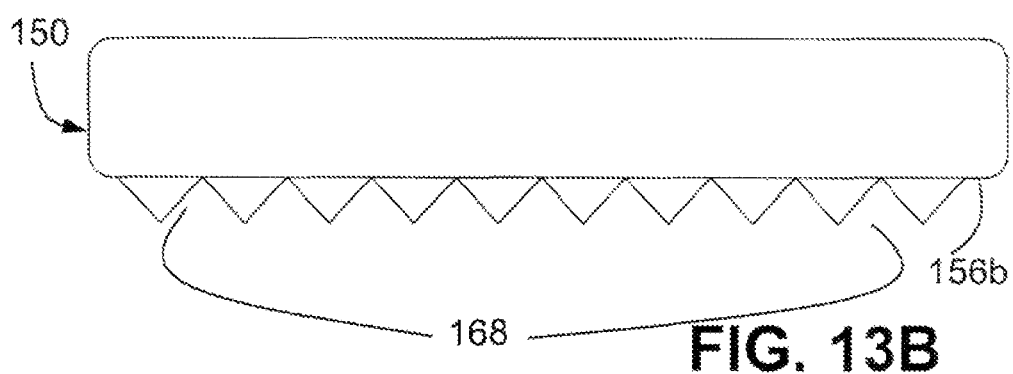

FIG. 13B shows a sensor face 156b having sharp ridges 168 which may be more suitable for reaching the skin through hair, than the nubs 166 of FIG. 13A. Sweat could also be channeled through the grooves in between the ridges 168.

Figure 13C:
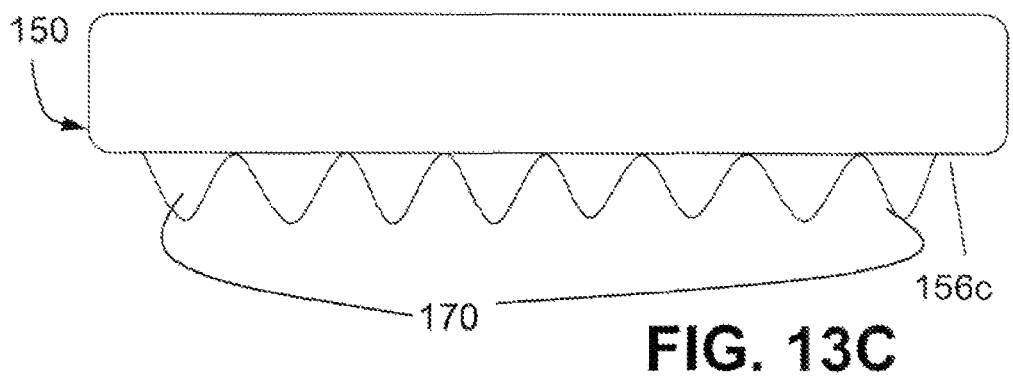
Figure 13D:
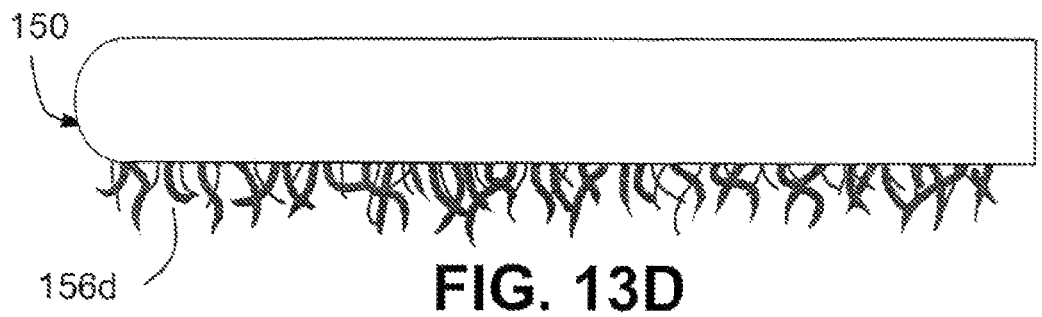

FIG. 13C shows another variation with grooves cut into the sensor face 156c forming softer ridges 170. In FIG. 13D conductive threads 172 are provided in the sensor face 158d and help maintain contact with the skin even when the sensor is sliding across the surface of the skin.

Figure 14A:
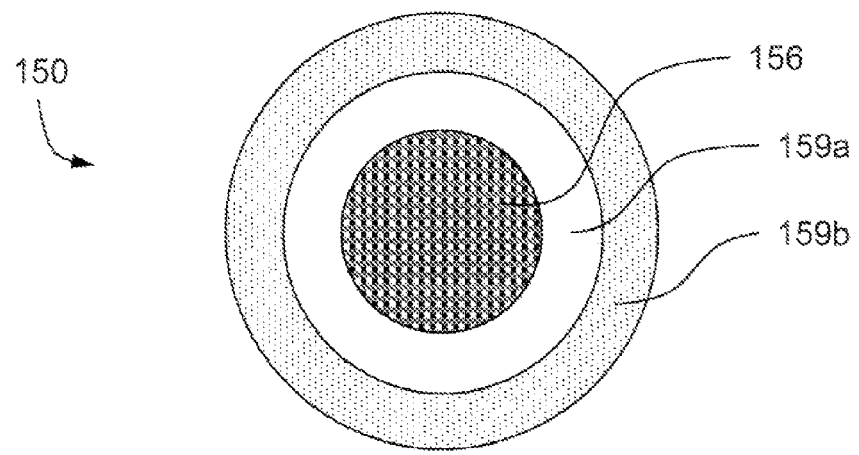
FIGS. 14A and 14B are plan views of a sensor.
Figure 14B:
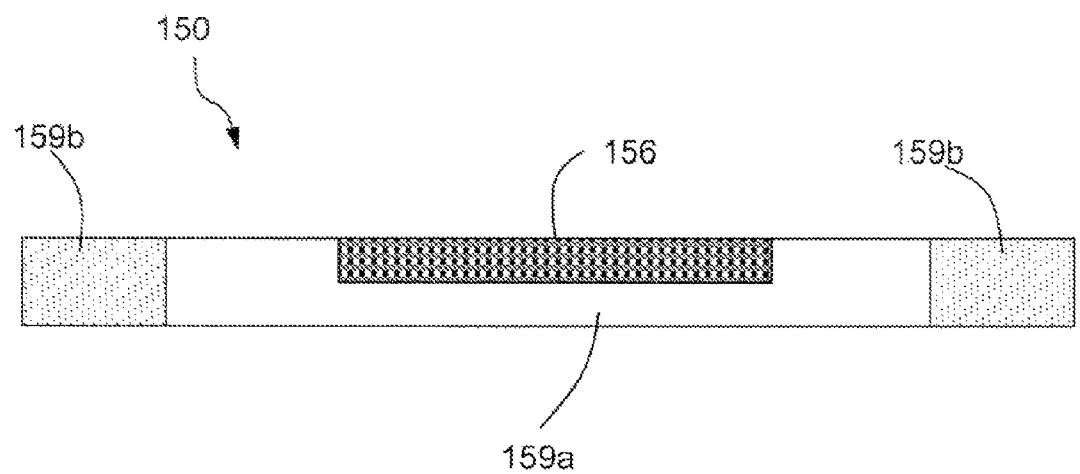

Referring to FIGS. 14A, 14B, a ring of material 159a could be placed around the sensing material 156 to provide one or two functions: to prevent the sensor from sliding by providing a high-friction material, and to induce sweat for better sensor conductivity by providing a water resistant material. Common wearable materials such as rubber and soft silicone provide both functions: they are high-friction and waterproof, which induces sweat.

Sweat is a good conductor for ECG sensors, and inducing a little sweat can help maintain skin contact and conductivity. However, if there is too much sweat, the sensor may slide against the skin, inducing noise in the signal, and the excess sweat may be uncomfortable. For this reason it may be beneficial to have a sweat absorbing ring 159b that surrounds the rest of the sensor. The sweat-absorbing material 159b can be made of cotton, for example.

The sensing material may be in the shape of a flat disk, as shown in FIG. 14A, and made of a conductive fabric which can absorb some sweat. These fabrics can tend to dry out when the user is not perspiring, which may drastically reduce the sensor's conductivity. One solution is to apply a waterproof or water resistant backing 159a to the sensing material 156, to help keep the sensing material 156 damp by sweat. The material 159a extends beyond the edges of the sensing material 156 to make contact with the skin and provide the high-friction function, while also providing a water resistant barrier around the sensing material 156 to induce sweat. For applications where large amounts of sweat are anticipated, the sweat disk 159a could be constructed of water resistant material that allows some evaporation. The sweat-absorbing ring 159b shown in FIG. 14B does not overlap any other part of the sensor, but is a separate ring to ensure direct skin contact and prevent sweat from dripping down from the sensor.

The sensing material 156, friction ring 159a and sweat-absorbing ring 159b are shown as circular shapes. However, other shapes such as rectangular can be used or the rings can be provided in alternating strips and so forth.

The ideal physiological sensor would be able to induce enough sweat for good conduction, but wick away excess sweat. In the absence of the ideal, users may desire to have different sensors for different activities, different amounts of sweat, and differences in comfort. Users may differ in how dry their skin is, how much body hair they have, or how much they sweat, requiring different sensors. To work in the presence of sweat or hair, an uneven surface will allow parts of the sensor to reach the skin and make good contact.

Figure 15:
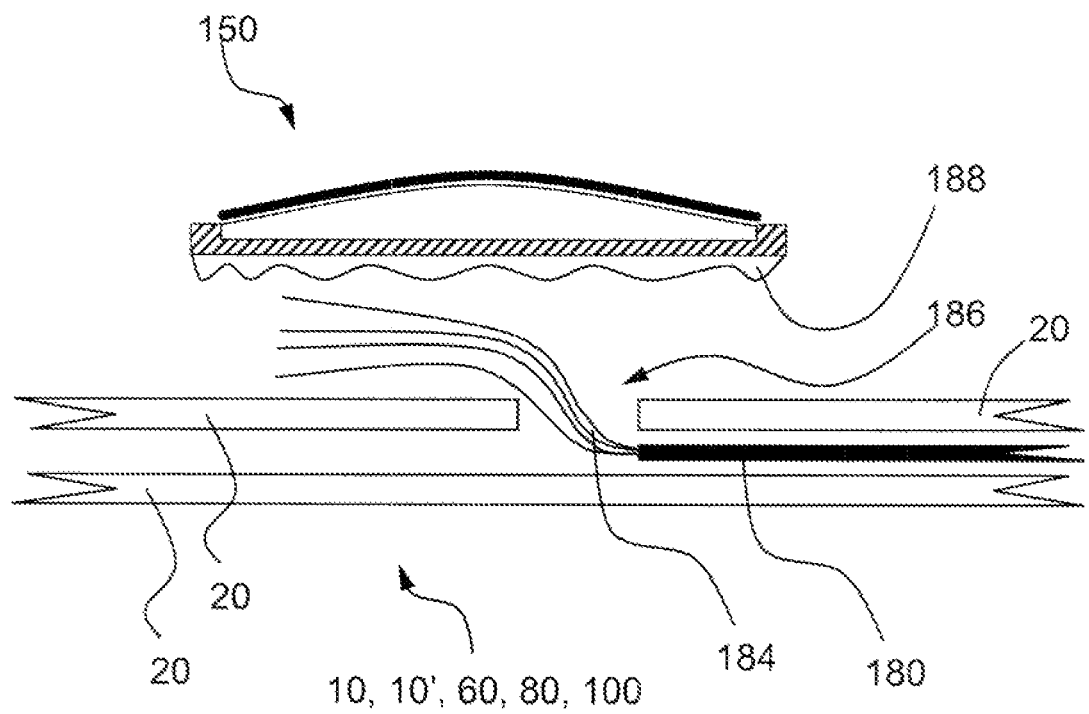
FIG. 15 is a cross-sectional view depicting wiring coupled to a sensor.

Referring now to FIG. 15, construction details of a garment with a sensor 150 in the process of being permanently attached, and an example of the associated integrated sensor wiring is shown. The garment, e.g., harness 10, 10', 60, and 80 is made up in this example of two layers of material 20. Sandwiched between the two layers of material 20 is a wire 180 which, in addition to being insulated, may optionally be shielded. Shielding can be useful because wires in a garment can pick up electromagnetic interference (EMI) such as 60 Hertz line noise or radio interference. Shielding also extends over the outside of the garment over the area of the sensors (not shown) to protect the sensors from picking up EMI. Sensor shielding consists of a thin metal material, possibly fabric, which is electrically wired to the wire shielding.

The wire 180 includes metal conductors 184. The insulation and shielding (if any) are stripped from the end of the wire 180, leaving the bare conductors 184 exposed. These bare conductors 184 are threaded through an aperture 186 in the garment to attach to the sensor 150. One way to attach the sensor 150 is with conductive epoxy 188 which may first be applied to the back of the sensor 150. To construct the garment, the sensor 150 with epoxy 188 is pressed down upon the exposed conductors 184 and permanently attached to the material 20. The wire 180 can be laid in the material 20 in an S shape to allow for the stretching of the garment.

The garments or harness 10, 10', 60 and 80 are wearable and may be relatively comfortable for wearing all day or while sleeping, for extended periods of time. The harness material, being flexible and somewhat elastic, imparts some comfort in the wearing of the harness. The sensors are comprised of skin-friendly materials, e.g., materials chat generally do not irritate the skin and are flexible next to the skin, increasing the sense of comfort. The wiring from each sensor would be integrated into the garment, e.g., harness. Besides its comfortable tactile properties, comfort of the garment is enhanced by its thin and lightweight construction. It is wearable in everyday use because it is non-bulky and therefore inconspicuous under most clothes.

The garments or harness 10, 10', 60 and 80 have comfortable sensors that do not use adhesive against the skin and yet can stay in place against the skin. The mechanisms that make this possible include a tensile force imparted to the sensors to hold the sensors against the body by the garments or harness 10, 10', 60 and 80, and also in some embodiments a high-friction material that tends to stay in place against the body. The garments or harness 10, 10', 60 and 80 allow sensors to be placed at physiologically useful places on the body, but also allow body movement that results in minimal stretch of the garment (for example, shoulder straps are close to the neck, so that arm movements result in minimal stretching of the shoulder straps). The sensors may also have a slightly sticky or tacky surface to help hold them in place.

The harnesses 10, 10', 60 and 80 have a minimal amount of fabric (as compared to a T shirt with integrated sensors, for example), so there is minimal force on sensors as a response to body movement. If a sensor should become unusable during exercise because of noise problems, the garments have the capability of providing multiple independent ECG leads.

For user convenience, the garments are washable, e.g., Neoprene is commonly used in wetsuits and is washable. The wearable sensor materials (with the exception of the hydrogel which absorbs water) including conductive rubber, conductive silicone and metallized fabric are all washable. Wiring can be covered with a waterproof sheath of, e.g., a plastic. The electronics can be "potted" in an RTV or the potting material and permanently integrated into the garment, or can be made removable from the garment. If removable, the garment's connector to the electronics could be covered with a waterproof cover to allow washing.

A number of embodiments of the invention have been described. Nevertheless, it will be understood that various modifications may be made without departing from the spirit and scope of the invention.

What is claimed is:

1. A garment comprising:
    a belt that is configured to be worn around a user's chest, the belt having a pair of ends with closures disposed at the pair of ends of the belt;
    at least one strap of unitary construction having a first end connected to the belt at a first front side of the belt and a second end, with the belt having a first accommodation and the at least one strap having a second accommodation, both the first accommodation and the second accommodation being configured to carry a sensor and with material that comprise both the belt and the at least one strap being a polychloroprene synthetic rubber to provide the garment for those portions configured to rest against the skin of the user wearing the garment with a high level of adherence against the skin, stretching, but not sliding over the surface of the skin; and
    a back portion having a broad region that is substantially greater in width in comparison with a width of the at least one strap and less than a width of the user's back and configured to rest against the back of the user, with an upper portion of the broad region joining the second end of the at least one strap, and with a lower portion of the back portion integrally joined with the belt;
    wherein the at least one strap couples between the belt and the back portion in a manner that the at least one strap diagonally traverses the chest of the user.

2. The garment of claim 1 wherein the first end of the at least one strap is removably coupled to the belt.

3. The garment of claim 1 wherein the second accommodation is attached in a region of the at least one strap that contacts a shoulder of the user.

4. The garment of claim 1 further comprising:
    a first conductor configured to attach to the sensor and a second conductor configured to attach to the sensor when the sensor is carried by the first accommodation or the second accommodation, the first conductor and second conductor being integrated into the garment.

5. The garment of claim 1 wherein the garment further comprises:
    the sensor carried by the first accommodation, wherein the sensor that is selected from the group consisting of an ECG sensor, motion sensor, body temperature sensor, respiration sensor and impedance plethysmography sensor.

6. The garment of claim 5 wherein the sensor has an uneven surface having at least one of the features of nubs, bumps, ridges, grooves or conductive threads to maintain contact with the skin of the user when sliding over the surface of the skin.

7. The garment of claim 1 wherein the garment further comprises:
    a stiffener member to hold the pair of ends of the belt forward of the user's body, when the belt is being put on and before it is fastened by the user.

* * * * *